United States Patent [19]

Miller

[11] 4,221,212
[45] Sep. 9, 1980

[54] METHOD OF IMPLANTING HAIR

[75] Inventor: Paul W. Miller, Atlanta, Ga.

[73] Assignee: Hairegenics, Inc., Atlanta, Ga.

[21] Appl. No.: 23,614

[22] Filed: Mar. 26, 1979

Related U.S. Application Data

[62] Division of Ser. No. 819,675, Jul. 28, 1977, abandoned.

[51] Int. Cl.² ............................................. A61B 17/00
[52] U.S. Cl. ..................................... 128/1 R; 128/330
[58] Field of Search .................. 128/330, 329 R, 1 R; 3/1; 46/172; 132/5, 53, 56

[56] References Cited

U.S. PATENT DOCUMENTS

| 527,263 | 10/1894 | Blanchard | 128/339 |
| 2,253,635 | 8/1941 | Mann | 132/56 |
| 3,032,923 | 5/1962 | Von Sternberg | 46/172 |
| 3,513,860 | 5/1970 | Kost | 132/56 X |
| 3,998,230 | 12/1976 | Miller | 128/330 |
| 4,004,592 | 1/1977 | Yamada | 128/330 |

FOREIGN PATENT DOCUMENTS 1953026  2/1972  Fed. Rep. of Germany ........... 128/330

Primary Examiner—William E. Kamm
Assistant Examiner—Michael H. Thaler
Attorney, Agent, or Firm—Robert B. Kennedy

[57] ABSTRACT

A method of implanting hair into skin tissue comprising the steps of forming an open loop on the end of a hair; passing the open hair loop over the tip of a needle and into hooked engagement within a notch formed in the needle periphery; inserting the needle and hair loop hooked thereto into skin tissue; releasing the hooked hair loop from the needle; and extracting the needle from the skin tissue.

3 Claims, 5 Drawing Figures

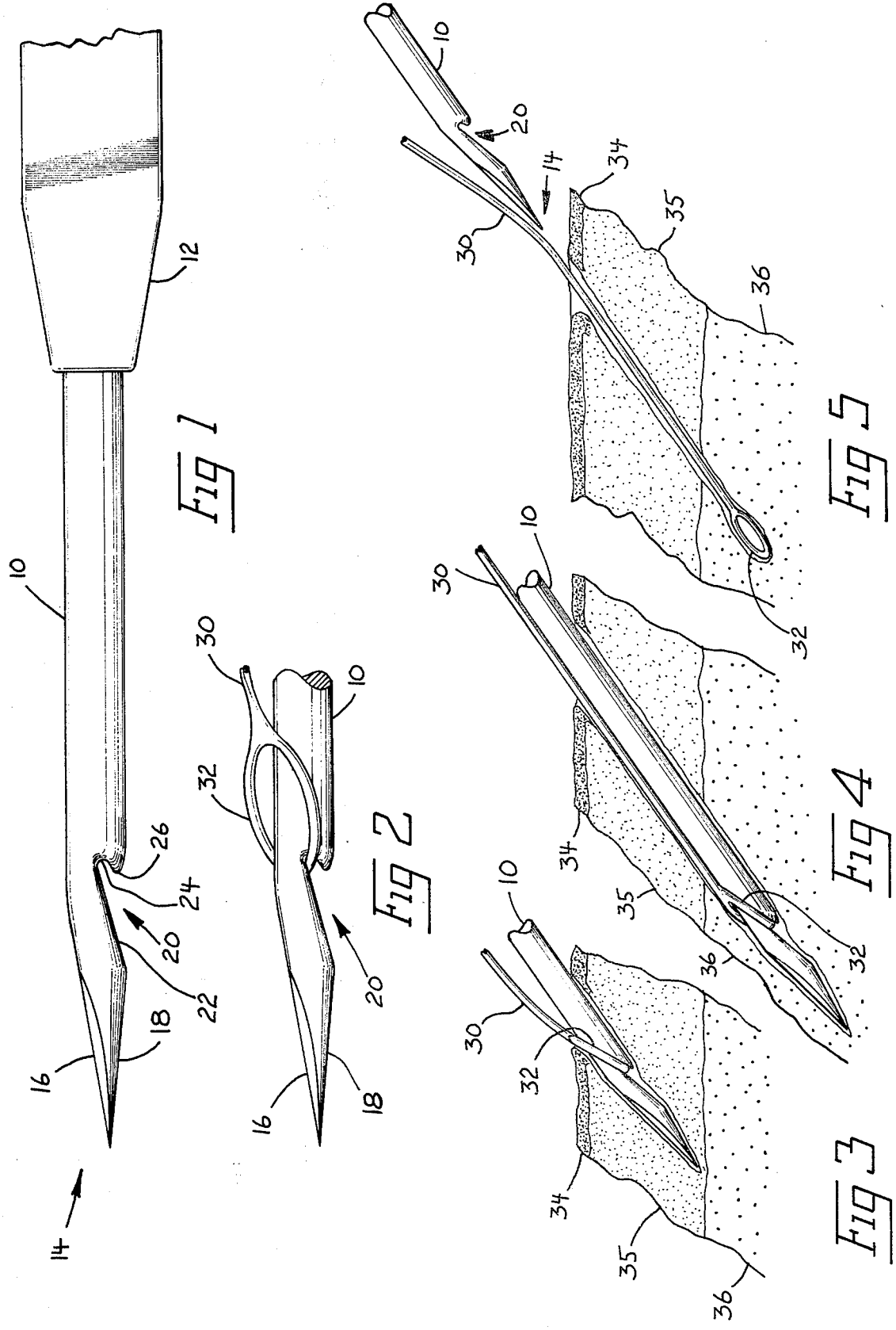

METHOD OF IMPLANTING HAIR

REFERENCE TO RELATED APPLICATION

This is a division of U.S. Patent Application Ser. No. 819,675 filed July 28, 1977 now abandoned.

BACKGROUND OF THE INVENTION

This invention relates generally to methods of implanting hair into skin tissue, and particularly to methods of implanting natural or synthetic hairs having an open loop formed on an end thereof into skin tissue.

In U.S. Pat. No. 3,998,230, which is assigned to the assignee of the present invention, a method of implanting a hair into skin tissue is disclosed wherein an open loop is formed on the end of a hair to be implanted through which skin tissue may subsequently grow and thereby tenaciously anchor the hair in place. The implantation operation itself is performed with apparatus having two hollow, mutually telescoping needles. The open loop is seated on an end of the inner needle with the hair extending therethrough. The outer needle is then inserted into skin tissue and the inner needle slid therewithin to place the open loop adjacent the outer needle tip. The outer needle is then withdrawn from the tissue over the hair loop and inner needle. The inner needle is then withdrawn leaving the hair loop implanted through which skin tissue may subsequently grow.

Though the just-described method and apparatus has proven satisfactory, it has not been problem free. For example, double telescoping needles must ordinarily be of larger gauge than single needles. The thicker the needle the more traumatic its use which results in greater scarring. In addition, the fact that each hair must be passed through the bore of the inner needle has limited needle loading and preparation efficiency.

In an effort to overcome the just described problems improved apparatuses and methods have been devised as disclosed in U.S. Pat. No. 4,126,124 which is also assigned to the assignee of the present application. Here a notch is formed in the hollow tip of a needle. Again the end of a hair is provided with an open loop which is seated in the hollow needle tip and the hair passed out through the notch and axially along the needle periphery. This has facilitated needle loading and has made the use of double telescoping needle assemblies unnecessary. Nevertheless, to insure that the open loop remains lodged in place upon needle extraction, the use of an inner, telescoping push rod has proven necessary to insure reliability. Furthermore, as with telescoping needles the open loop has had to be carried within the confines of a needle which has often caused it to collapse and to remain collapsed once implanted thereby inhibiting the growth of skin tissue therethrough.

Accordingly, it is a general object of the present invention to provide improved methods of implanting hair into skin tissue.

More specifically, it is an object of the invention to provide improved methods of implanting a natural or synthetic hair having at least one open loop formed on the end thereof into skin tissue.

Another object of the invention is to provide methods of the type just described by which a hair may be loaded onto an implantation needle with enhanced loading facility and efficiency.

Another object of the invention is to provide methods of the type described with reliability that hair loops will remain open during implantation and will remain in place and not be partially or totally withdrawn upon needle extraction.

Yet another object of the invention is to provide methods of the type described which do not mandate use of telescoping or hollow needles.

SUMMARY OF THE INVENTION

In one form of the invention a method is provided for implanting hair into skin tissue. The method comprises the steps of forming an open loop on the end of a hair and passing the open hair loop over the tip of a needle and into hooked engagement within a notch formed in the needle periphery. The needle and hair loop hooked thereto are then inserted into skin tissue, the hair loop released from the needle, and the needle extracted from the skin tissue.

BRIEF DESCRIPTION OF THE DRAWING

FIG. 1 is a side elevational view of hair implantation apparatus which may be used in practicing a method of the invention.

FIG. 2 is another side elevational view of an end portion of the apparatus illustrated in FIG. 1 shown with a hair loaded thereon.

FIG. 3 is a side view of the needle illustrated in FIG. 1 and loaded as illustrated in FIG. 2 shown penetrating skin tissue for implantation while;

FIG. 4 shows the loaded needle fully inserted and

FIG. 5 shows the needle extracted leaving a hair implanted.

DESCRIPTION OF THE PREFERRED EMBODIMENT

Referring now in more detail to the drawings, there is shown a needle 10 which preferably is of 27 to 30 gauge size. The needle here is of solid, generally cylindrical construction although such is not essential. The needle is mounted to a block 12 to which an unshown handle is secured. Preferably the block has sufficient width to support a plurality of needles side by side whereby a set of hairs may be implanted substantially simultaneously with predetermined spacings therebetween.

The tip 14 of the needle is sharp having a flat, beveled top surface 16 while the underside surface 18 is conical. The periphery of the needle adjacent tip 14 is seen to be provided with a notch 20. The notch is defined by a ramp surface 22 oriented generally parallel the tip beveled surface 16 sloping towards the needle axis which ramp merges with a rounded base surface 24 near the axis. The notch is further defined by a rounded lip 26 which is conjoined with ramp 22 by the base 24. The lip is seen to project towards the needle tip 14 thereby providing a hook.

So constructed a natural or synthetic hair may be loaded onto the needle for implantation as shown in FIG. 2. Here a 40 to 60 denier plastic filament 30 is seen to be formed with an open loop 32 on an end thereof of sufficient size to be passed easily over the needle tip. For increased anchoring tenacity the filament may be provided with more than one loop. If desired a natural hair may be used in lieu of a synthetic.

For loading loop 32 is simply passed over the needle tip and slid along conical surface 18 and notch ramp 22 onto base 24. With filament 30 extended axially over the periphery of the needle towards block 12 further movement of loop away from tip 14 is prevented by notch lip 26. In effect, loop 32 is now hooked in place. The filament 30 is preferably held tautly upon the block 30 as by means of a clip until implantation is begun.

With reference next to FIGS. 3-5 the steps involved in implanting a hair loaded as just described may be sequentially visualized. The needle tip is preferably inserted angularly into the two upper layers of human skin tissue 34 and 35 bringing hair loop 32 along with it into the skin. As a substantial portion of the loop lies within the peripheral notch the loop itself does not effect a substantial increase in the size of the skin puncture. Further penetration is effected bringing both the needle tip and notch into the lowermost layer 36 of the skin as shown in FIG. 4 with loop 32 retaining its preselected sized opening. Finally, the needle is extracted along its path of entry as shown in FIG. 5 by reverse movement. This action itself simultaneously causes the hair loop 32 to slide along ramp 22 out of notch 20 thereby unhooking the loop from the needle. As the skin tissue closes into the passageway made by the departed needle it converges upon the hair loop and filament. Subsequently skin tissue will grow through loop 32 and firmly anchor the hair in place.

It should be understood that the just described embodiment merely illustrates principles of the invention in a preferred form. Many modifications, additions and deletions may, of course, be made thereto without departure from the spirit and scope of the invention as set forth in the following claims.

I claim:

1. A method of implanting hair into skin tissue comprising the steps of
    (a) forming a loop completely encircling an opening on the end of a hair;
    (b) passing the opening encircling loop over the tip of a needle and into hooked engagement within a notch formed in a side of the needle adjacent the needle tip;
    (c) inserting the needle and hair loop hooked thereto into skin tissue; (d) releasing the hooked hair loop from the needle; and (e) extracting the needle from the skin tissue.

2. The method of implanting hair in accordance with claim 1 wherein step (c) the needle and hair loop hooked thereto are inserted into skin tissue with the hair extending along the periphery of the needle away from the needle tip.

3. The method of implanting hair in accordance with claim 1 wherein step (d) is effected by step (e).

* * * * *